United States Patent
Barclay et al.

(10) Patent No.: US 6,190,917 B1
(45) Date of Patent: Feb. 20, 2001

(54) MICROWAVE APPARATUS AND METHOD FOR ANALYSIS OF ASPHALT-AGGREGATE COMPOSITIONS

(75) Inventors: David Allan Barclay, Charlotte; Ali Regimand, Raleigh, both of NC (US)

(73) Assignee: CEM Corporation, Matthews, NC (US)

( * ) Notice: Under 35 U.S.C. 154(b), the term of this patent shall be extended for 0 days.

(21) Appl. No.: 09/045,392

(22) Filed: Mar. 20, 1998

(51) Int. Cl.[7] ............ G01N 31/12; G01N 33/26; H05B 6/64

(52) U.S. Cl. ............ 436/60; 219/710; 219/712; 219/756; 219/757; 219/762; 422/68.1; 422/78; 422/99; 422/109; 436/139; 436/140; 436/141; 436/142; 436/143; 436/145; 436/155; 436/157; 436/160; 436/181; 436/183; 436/55

(58) Field of Search .............. 436/60, 139, 140, 436/141, 143, 145, 147, 155, 157, 160, 174, 181, 183, 55; 422/68.1, 78, 99, 109, 288, 307; 219/710, 712, 756, 757, 762, 697

(56) References Cited

U.S. PATENT DOCUMENTS

| | | |
|---|---|---|
| 4,043,048 | 8/1977 | Veater . |
| 4,164,655 | 8/1979 | Noma et al. . |
| 4,307,277 * | 12/1981 | Maeda et al. .............. 219/10.55 |
| 4,525,854 | 7/1985 | Molbert et al. . |
| 4,565,669 * | 1/1986 | Collins et al. .............. 422/78 |
| 4,849,020 | 7/1989 | Osborne et al. . |
| 4,874,950 | 10/1989 | Regimand . |
| 4,990,456 | 2/1991 | Loucks et al. . |
| 5,066,843 * | 11/1991 | Revesz .............. 219/10.55 R |
| 5,151,601 | 9/1992 | Regimand . |
| 5,170,667 | 12/1992 | Takeuchi et al. . |
| 5,248,200 | 9/1993 | Walsh . |
| 5,279,971 * | 1/1994 | Schneider .............. 436/139 |
| 5,318,754 * | 6/1994 | Collins et al. .............. 422/109 |
| 5,365,043 * | 11/1994 | Bradford .............. 219/710 |
| 5,378,878 * | 1/1995 | Revesz .............. 216/762 |
| 5,558,029 | 9/1996 | Peake . |
| 5,796,080 * | 8/1998 | Jennings et al. .............. 219/697 |

FOREIGN PATENT DOCUMENTS 2261827   6/1993  (GB) .

OTHER PUBLICATIONS

F. Parker Jr. *J. Test Eval.* 1991, 19, 161–168.*
L. Drüschner *Bitumen* 1993, 55, 158–162.*
H.A. Todres et al. *J. Test. Eval.* 1994, 22, 564–570.*
E.R. Brown et al. *Asphalt Paving Technol.* 1995, 64, 241–277.*
S. Kocakusak et al. *NATO ASI Ser., Ser. E* 1995, 282, 351–358.*
M. Thomsen et al, *At. Spectrosc.* 1998, 19, 60–61.*
G. Gowda et al, in "Mater. New. Millennium", Proc. Mater. Eng. Conf. American Society of Civil Engineers: New York, vol. 1, pp. 612–621.*

* cited by examiner

Primary Examiner—Arlen Soderquist
(74) Attorney, Agent, or Firm—Philip Summa, P.A.

(57) ABSTRACT

A method and apparatus are disclosed for analyzing asphalt-aggregate compositions. The method includes directing sufficient microwave radiation from a microwave source to a sample of an asphalt-aggregate composition to ignite the asphalt in the composition and to thereafter entirely combust the asphalt in the sample. The apparatus includes a source of microwave radiation, a cavity in communication with the microwave source, a sample holder in the cavity for holding a sample of an asphalt-aggregate composition during exposure to microwaves from the source, thermal insulation between the sample holder and the remainder of the cavity, and means for minimizing or eliminating any undesired combustion products generated by the burning asphalt.

19 Claims, 2 Drawing Sheets

MICROWAVE APPARATUS AND METHOD FOR ANALYSIS OF ASPHALT-AGGREGATE COMPOSITIONS

FIELD OF THE INVENTION

The present invention relates to the analysis of compositions formed of asphalt and aggregates such as crushed rock and sand. In particular, the invention relates to a method and apparatus for analyzing the percentage composition of asphalt in such compositions.

BACKGROUND OF THE INVENTION

Compositions formed of mixtures of asphalt and aggregates materials are one of the most widely used materials for paving roads and highways. Although the term "asphalt" is commonly used to refer to the road material, it more properly applies to the "tar" portion of a mixed composition of tar and aggregate. Thus, the asphalt is a dark brown or black cementitious material, which is solid or semi-solid in consistency, in which the predominating constituents are bitumens which occur in nature or are obtained as byproducts from petroleum refining. Asphalt is a mixture of paraffinic and aromatic hydrocarbons and heterocyclic compounds containing sulfur, nitrogen and oxygen. Asphalt is also referred to as "petroleum asphalt," "Trinidad pitch," or "mineral pitch." Asphalt is a black solid or viscous liquid that has a flash point of about 450° F. and an auto-ignition temperature of about 900° F. (482° C.) and softens from its solid or semi-solid state to a viscous liquid at approximately 93° C. Other typical uses of asphalt include roofing, joint filling, special paints, adhesive and electrical laminates, and hot belt compositions, a diluent in low-grade rubber products, and a number of other applications. These and other properties and uses of asphalt are generally well known in the art and can be found, for example, in Lewis, *Hawley's Condensed Chemical Dictionary*, 12th Edition (1993).

In paving compositions, asphalt is typically present in an amount of about 5% by weight. With respect to such compositions, the percentage of asphalt and the nature and size of the aggregate material (typically rocks and sand) used to make the composition are important for the proper structure and characteristics of the final road structure. For example, typical roads are formed of three layers of asphalt and aggregate compositions. The bottom most layer includes rocks of one inch or greater average size, sand, and the asphalt. An intermediate layer typically includes a composition formed of somewhat smaller rocks, typically 0.5–1 inch in diameter, again with sand and asphalt. Finally, a top layer is usually applied which has the smallest rocks, typically 0.5 inches or less in diameter plus sand and tar.

Because the aggregate generally represents more than 90% of a hot asphalt mix, aggregate gradation (i.e., the different particle sizes that are present in the blend) profoundly influences the properties of the hot mix (such as air voids, workability, and the amount of asphalt binder required) and the resulting properties of the pavement (such as stiffness, stability, and durability) (e.g., Aljassar et al., *Toward Automating Size-Gradation Analysis of Mineral Aggregate*, Transportation Research Record, Issue Number: 1437, pp. 35–42 (1994)). In this regard, research on asphalt-aggregate compositions has become quite detailed, including for example quantifying the influence on resistance to rutting when rounded, smooth, sand-sized aggregate particles are replaced by rough, angular, porous particles while other aggregates and the total gradation remain unchanged (e.g., Perdomo, D. and Button, J. W., *Identifying and Correcting Rut-Susceptible Asphalt Mixtures, Final Report*, Texas Transportation Institute, Texas A&M University, Texas State Department of Highways & Public Transp, Federal Highway Administration, Report Number: Fhwa/Tx-91/1121-2F;Res Rept 1121-2F;TTI: 2-8-87/91-1121, Pag: 164p), or evaluating the effect of the amount of soil binder (i.e., the smallest aggregate particles) on the engineering properties of asphalt-treated paving materials (Ping, and Kennedy, *The Effects of Soil Binder and Moisture on Black Base Mixtures*, Texas University, Center for Highway Research, Austin, Texas State Department of Highways & Public Transp Report Number: FHWA/TX79/08+183-12 Intrm Rpt.;FCP 45C2-352 Pag: 127p (1997)). Aggregate gradation is frequently determined by the well-known and widely used sieve analysis method.

Accordingly, as these exemplary references indicate, depending upon the conditions under which a road is used (e.g., traffic patterns and weather conditions), the composition of any one or more of the asphalt layers must be carefully designed and monitored. Additionally, because the aggregate materials are typically taken from local quarries, and the manufacture of the composition is not an exact science, the asphalt and aggregate compositions must be frequently tested, both as they are being made and after they have been applied to a roadway, to make sure that they meet the appropriate requirements.

Thus, there exists a need for determining: (1) the weight percentage of asphalt; and (2) the aggregate size distribution in a given sample of an asphalt-aggregate composition. In one conventional method of analysis, the percentage of asphalt is determined by a solvent extraction technique which uses chlorinated hydrocarbons to separate the asphalt from the aggregate materials. Because the solvents are generally considered to raise a hazard to persons who are exposed to their vapors, the solvent testing is becoming more and more disfavored, and indeed is expected to eventually become prohibited under appropriate environmental regulation.

In a second conventional method, a weighed sample of the composition is placed into a furnace which is then heated until the asphalt in the composition ignites. The asphalt is then allowed to burn until it is entirely consumed after which the remaining aggregate is weighed. The difference between the starting and ending weight is a measure of the composition of asphalt in the composition.

There are, however, at least two problems with this conventional ignition technique. First, in conventional conduction and convection heating, the burning asphalt can carry the combustion to temperatures of up to 900° C., i.e., a state which is somewhat out of control. These extreme temperatures can cause particular problems in the equipment or in handling the hot material or even confirming the resulting fire.

Second, and perhaps just as important, the extreme temperatures tend to degrade the physical characteristics of the aggregate in the mixture, including its size. Thus, because the aggregate remaining after the asphalt has been burned off is typically measured to determine whether it is of the proper size, the size degradation resulting from the conventional ignition test leads to a certain inaccuracy in measuring the sizes of aggregate in any given sample.

As another problem, if the aggregate contains carbonate compounds, the excessive heat can drive off carbon dioxide, thus changing both the chemical and physical characteristics of the aggregate. Finally, the conventional ignition techniques tend to cause a loss of "fine" aggregates—literally blowing them away—so that such fines are neither sized nor weighed, further acerbating the accuracy problem.

Accordingly, the need exists for a method of determining the amount of asphalt in an asphalt-aggregate combination which avoids the use of environmentally disfavored solvents, which more carefully controls the combustion and which avoids the breakdown in the aggregate materials that tends to result in improper sizing following such testing.

OBJECT AND SUMMARY OF THE INVENTION

Therefore, it is an object of the present invention to provide an approved method and apparatus for analyzing asphalt-aggregate compositions.

The invention meets this object with a method of analyzing asphalt-aggregate compositions in which sufficient microwave radiation is directed from a microwave source to a sample of an asphalt-aggregate composition to ignite the asphalt in the composition and to thereafter entirely combust the asphalt in the sample. In preferred embodiments the microwave radiation is moderated as is the oxygen available to the sample to maintain the temperature of the ignited composition within the controllable range. In further embodiments of the invention, the weight of the sample is measured before and after the combustion of the asphalt, and the remaining aggregate is sized to determine it particle size distribution.

In another aspect, the invention comprises an apparatus for analyzing the asphalt content of an asphalt-aggregate composition. The apparatus comprises a source of microwave radiation, a cavity in communication with the microwave source, a sample holder in the cavity for holding a sample of an asphalt-aggregate composition during the exposure to microwaves from the source, thermal insulation between the sample holder and the remainder of the cavity and means for minimizing or eliminating any undesired combustion products generated by the burning asphalt.

The foregoing and other objects and advantages of the invention and the manner in which the same are accomplished will become clearer based on the following detailed description taken in conjunction with the accompanying drawings in which:

DETAILED DESCRIPTION

Figure 1:
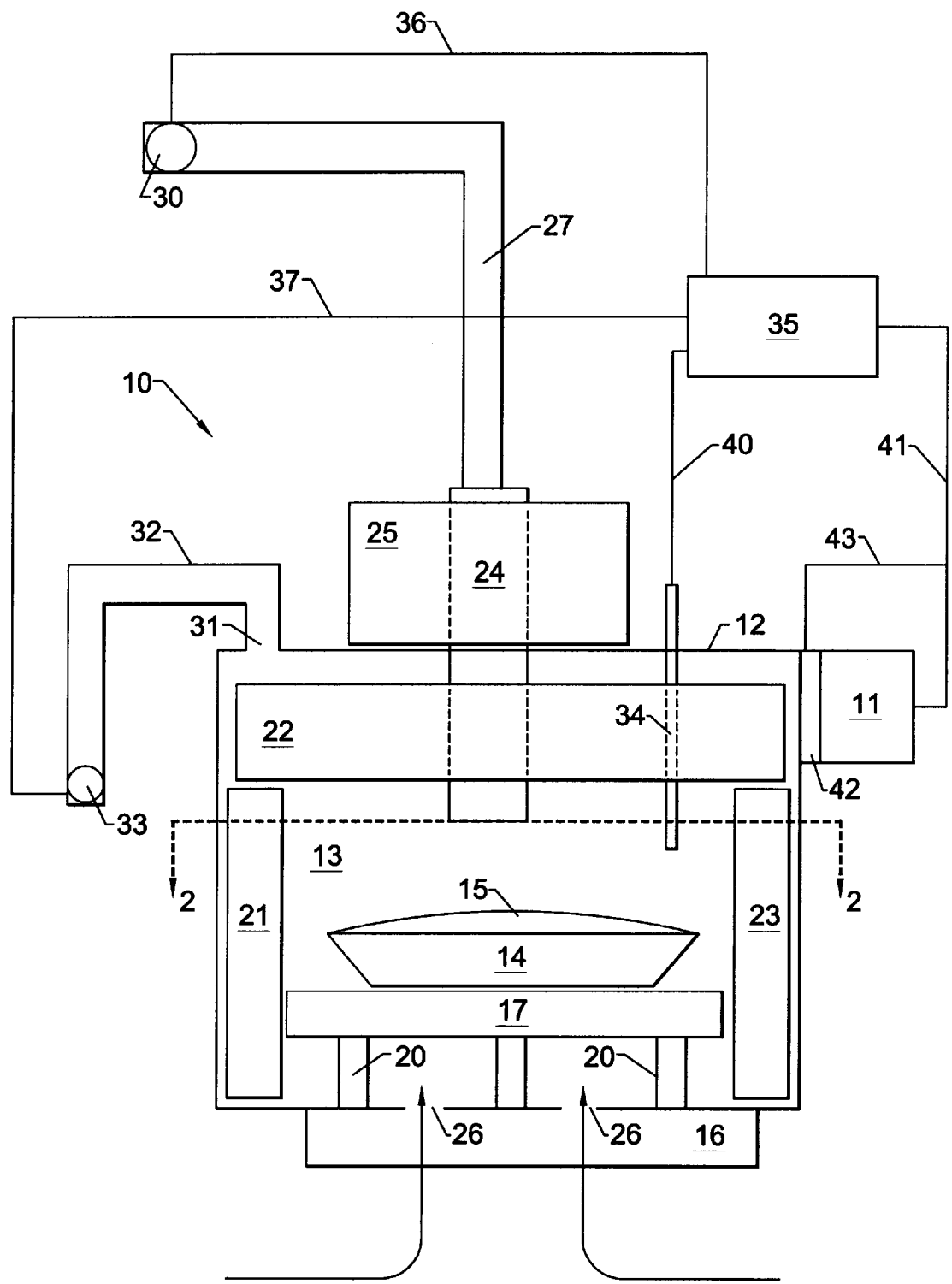
FIG. 1 is a schematic cross-sectional representation of the apparatus according to the present invention.

In the first embodiment, the invention is a method of analyzing asphalt-aggregate compositions comprising directing sufficient microwave radiation from a microwave source to a sample of an asphalt-aggregate composition to ignite the asphalt in the composition and to thereafter entirely combust the asphalt in the sample. Because one of the objects of the invention is to determine the weight percentage of asphalt in the composition, the method preferably further comprises weighing the sample before and after combustion to provide the data needed to calculate weight loss and percentage asphalt. These are, of course, very straightforward calculations and are usually taken by measuring the difference between the starting and the finishing weight, dividing the difference by the starting weight of the sample, and then expressing the answer either as a decimal fraction or a percentage.

As noted above, one of the most important characteristics of an asphalt-aggregate composition is the particle size distribution of the aggregate materials. Thus, the method of the invention further comprises sizing the aggregate after combustion of the asphalt. In particular, the nature of the combustion process according to the invention provides a less distorted and frequently undistorted aggregate for which the sizes and size distribution can be more accurately determined.

In preferred aspects of this embodiment, the method comprises directing microwave radiation from the source to the sample until the composition ignites, then moderating the microwave radiation directed to the sample and the amount of oxygen available to the sample to maintain the temperature of the ignited composition within a controllable range, and then reducing the gaseous combustion products substantially to carbon dioxide and water vapor.

In order to prevent the ignited asphalt from burning out of control, the step of moderating the microwave radiation preferably comprises measuring the temperature of the sample during combustion and then moderating the amount of microwave radiation applied based on the measured temperature. It will be understood that the temperature can be measured either in or near the sample and that the resulting measurements will provide essentially equivalently useful information. Given the rapid interaction of microwaves with materials, and the fact that microwave power can be immediately stopped, as opposed to convection or conduction heating which tend to continue until thermal equilibrium is reached, the method provides an increased amount of control over asphalt ignition and combustion reactions than has previously been available. Stated in somewhat simplified fashion, the combustion can be started and stopped more quickly than with conventional techniques and devices.

In preferred embodiments, the interaction between the microwaves and the asphalt-aggregate composition is not the sole source of heating. Instead, the method further comprises placing one or more susceptors within the furnace that also absorb microwave energy and convert it into heat. The susceptors are formed of one or more materials that will both absorb microwaves and convert them into heat, with silicon carbide (SiC) being an efficient choice for the material. Preferably, the SiC susceptors are present in an amount, and in selected positions, sufficient to raise the temperature inside the furnace to at least about 540° C., even in the absence of a sample. In a preferred embodiment of the method, the SiC susceptors are placed in the furnace and microwaves are applied to the susceptors until they heat the furnace to about 540° C., after which the sample is added. The size and number of susceptors is also selected as to optimize the control of the combustion reaction after ignition, and to help complete the later stages of the combustion process after the rapidly-burning components of the composition have been consumed.

In a preferred embodiment, the invention further comprises the method of controlling the airflow to the sample to thereby moderate the oxygen available and control the combustion following ignition. In preferred embodiments, the method comprises measuring the temperature of the burning sample and controlling the airflow in response to the measured temperature.

In this regard, the airflow can be used to either accelerate or decelerate the combustion. Because asphalt is a mixture of hydrocarbons with different properties, its initial ignition tends to generate a rapid combustion of the highly volatile and highly flammable portions, followed by a slower and more deliberate combustion of the remaining portions. Accordingly, airflow can be decreased to moderate the rapid combustion and increased to encourage the slower combustion.

In other aspects of the method, the step of reducing the byproducts comprises carrying out a follow up combustion step on the gaseous byproducts to more completely reduce them to carbon dioxide and water vapor. The follow-up combustion step is typically carried out in an afterburner which will be described in more detail with respect to the apparatus aspects of the invention.

For control purposes, the microwave power that reaches the sample can be moderated by moderating the amount of microwave produced in the source, or by moderating their passage between the source and the sample.

In another aspect, the invention comprises a method of analyzing composition road building materials which comprises weighing a sample of an asphalt-aggregate composition, directing sufficient microwave radiation from a microwave source to a sample of an asphalt aggregate composition to ignite the asphalt in the composition, thereafter continuing to direct microwave radiation to the sample until the asphalt in the sample is entirely combusted, weighing the sample after the asphalt has been entirely combusted, and sizing the aggregate. The sample to be measured is typically selected from existing road materials, portions of asphalt aggregate compositions that have just been produced, and portions of asphalt-aggregate compositions that are being produced; i.e., during the production process. In typical embodiments, the step of sizing the aggregate comprises sieve analysis (e.g., U.S. standard sieve sizes), but it will be understood that any appropriate sizing technique can be used with the present invention and that the invention provides the advantage of maintaining the aggregate in its original size following combustion much more successfully than have prior ignition techniques.

In another aspect the invention comprises an apparatus useful in carrying out the method of the invention. In FIG. 1, the overall apparatus is broadly designated at 10. The apparatus comprises a source of microwave radiation which is illustrated schematically at 11. The source is typically a magnetron because of its generally well-understood characteristics and reasonable cost. Those familiar with the generation of microwaves, however, will recognize that any appropriate microwave source could be incorporated, including klystrons, solid-state devices, and other microwave generators. Because the operation of these is generally well known and not otherwise limiting of the present invention, they will not be discussed in detail herein. It will also be understood that the source 11 is in communication with a cavity which is illustrated as the housing 12 in FIG. 1. In most embodiments, the source 11 will communicate with the cavity 12 through a waveguide, again in a manner well understood to those of ordinary skill in this art.

The housing 12 is typically formed of metal and defines the cavity 13 and provides a shield against the emission of microwave radiation from the cavity 13 when the cavity is receiving microwaves from the source 11. The particular metal and structural details of the housing 12 can be easily selected by those of ordinary skill in this art and without undue experimentation.

A sample holder 14 is positioned in the cavity for holding a sample 15 of the asphalt-aggregate composition that is being analyzed during exposure to microwaves from the source 11. The sample holder should be large enough to hold the necessary sample size desired for testing, and is preferably heat resistant and made of a material that is either transparent or minimally absorbent of microwave radiation and that can withstand the high temperatures generated after the sample 15 ignites. Typical materials can include stainless steel, aluminum, ceramic materials or combinations of these materials. Preferably, the sample holder 14 is perforated to permit a freer movement of air through the asphalt-aggregate mixture. Additionally, depending upon the circumstances and other factors, the sample holder can rotate on a turntable (not illustrated in this embodiment). In the illustrated embodiment, the apparatus includes a balance 16 for measuring the weight of the sample 15 in the sample holder 14 before, during and after combustion. The balance 16 includes the balance pan or platform 17, and the supports 20 that connect the pan 17 to the balance mechanism 16. Appropriate balance mechanisms and the manner of incorporating them into microwave devices are generally well understood in this art and can be selected and incorporated without undue experimentation. Additionally, those familiar with weighing heated objects in ovens will recognize the presence and effects of convection air currents, and will likewise be aware of the need to incorporate an appropriate correction factor into the weight calculations.

Figure 2:
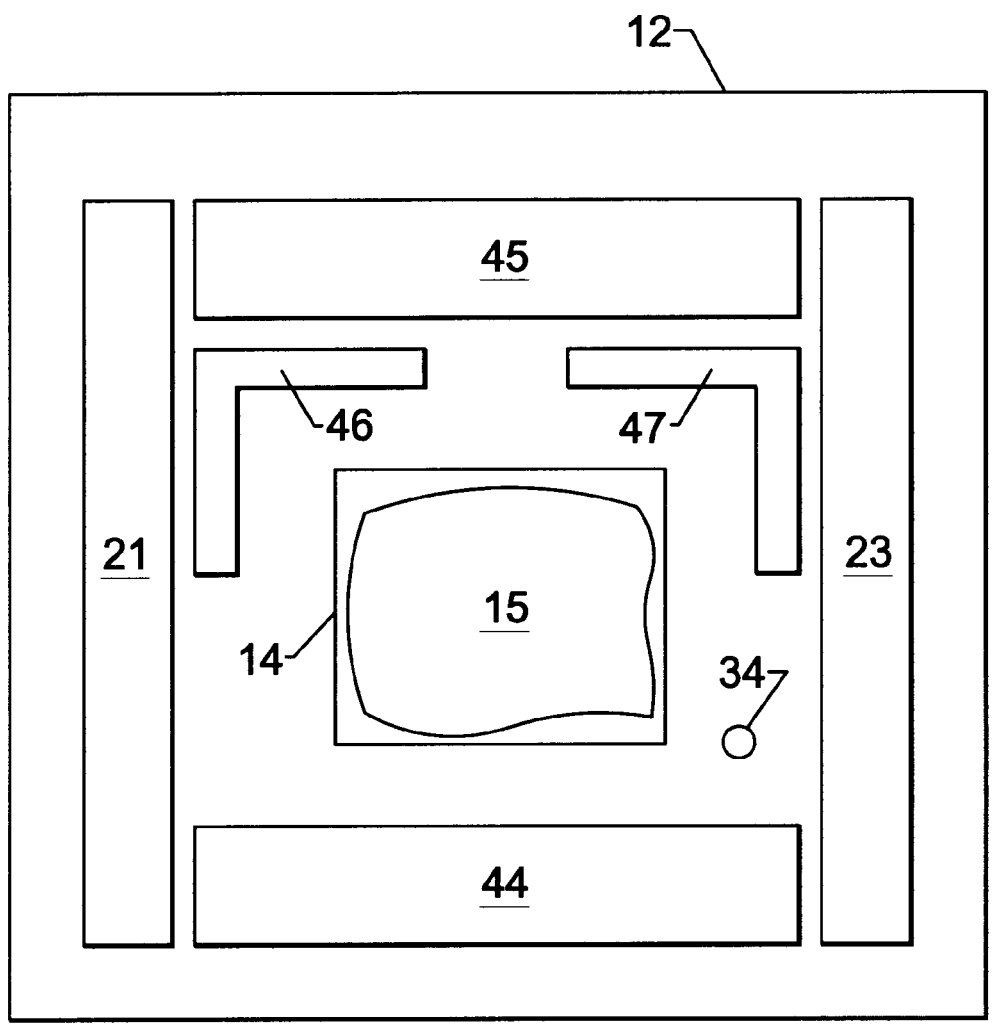
FIG. 2 is a top plan cross-sectional view of the apparatus taken along line 2—2 of FIG. 1.

The invention further comprises thermal insulation shown in the form of the three solid polygons 21, 22, and 23 in FIG. 1. The thermal insulating material completely surrounds the sample in the cavity 13 and forms the furnace in which the sample can ignite and burn without spreading to the ambient surroundings. As FIG. 1 illustrates, the thermal insulation and can be formed from a number of individual pieces, and it will be understood that there is at least one more piece covering the front and the back portions of the cavity 13 and that is not shown in FIG. 1 because it would otherwise obstruct the view of the remaining elements. FIG. 2 illustrates these pieces at 44 and 45. In preferred embodiments, the thermal insulation is heat resistant, microwave transparent and has a low thermal conductivity. Preferred materials both withstand the heat generated by ignition and combustion and also keep the heat from being transmitted to the housing 12 or to the ambient surroundings. Preferred materials include an open-cell quartz, and quartz or borosilicate glass fibers. The insulation and the structure it produces are quite similar to those referred to as "muffle" furnaces (e.g., U.S. Pat. No. 5,318,754 which is commonly assigned with the present invention) and will not otherwise be described in detail herein.

As set forth in the background portion of the specification, the asphalt portion of an asphalt-aggregate composition is formed of a wide variety of hydrocarbon materials and thus results in a similarly wide variety of combustion byproducts. According to the present invention, it has been determined that a preferred method of eliminating these undesired combustion products is to include an afterburner which in FIG. 1 is illustrated as the tubular furnace 24. The tubular furnace 24 is heated (typically to about 1000° C.) by any conventional process such as electric resistance heating, and is insulated from the ambient surroundings by the insulating material 25 which can be the same as that which forms the thermal insulation inside the cavity. In preferred embodiments, the apparatus includes means for directing the combustion products from the cavity 13 to the afterburner 24. In one preferred embodiment, the means for directing the combustion products to the afterburner include one or more openings 26 in the cavity in fluid (i.e., airflow) communication with the sample holder 14 and the sample 15, a duct 27 in communication with the downstream portion of the afterburner 24, and a fan schematically illustrated at 30 associated with the duct 27 and downstream from the afterburner 24 for drawing ambient air into the cavity 13 and for concurrently drawing the afterburner products away from the afterburner 24. In a particularly preferred embodiment, the invention will further comprise an additional opening 31 in the housing 12 outside of the thermal insulation 21, 22, 23 and leading to an additional duct 32 and fan 33 for drawing an additional portion of air through the cavity and through the housing. Using these fans, the amount of air being drawn through the cavity, and thus available for combustion of the sample 15, can be more carefully controlled. As noted above, during the early portions of combustion following ignition, the airflow may preferably be minimized to keep the combustion from getting out of control. Later in the process, when the combustion is moving more moderately or even relatively more slowly, the airflow can be increased to speed that part of the process along.

Accordingly, in preferred embodiments of the invention, the apparatus includes a temperature sensor 34 preferably positioned inside of the thermal insulation 21, 22, and 23 for determining the temperature in the portion of the cavity 13 inside of the thermal insulation, and thus serving to provide an appropriate means of monitoring the temperature of the sample 15 during combustion. If desired, the temperature sensor 34 could be placed entirely within the sample, but it has been determined that because the temperature within the boundaries of the insulation is closely representative of the combustion temperature, there is no particular need in most circumstances to directly contact the sample 15 with the temperature sensor 34.

The temperature sensor 34 can be selected as desired based on a number of engineering criteria, but will typically comprise of a thermometer, a thermocouple or an optical temperature measuring device. It will be understood that the particular device used to measure the temperature is in no manner limiting of either the apparatus or method of the present invention.

In preferred embodiments, the apparatus further includes means shown as the controller 35 for controlling microwave power or the airflow applied to the sample 15 based on the temperature detected by the temperature sensor 34. As schematically illustrated in FIG. 1, the controller can be connected to the fan 30 through the circuits schematically shown as 36, or to the fan 33 through the circuits schematically illustrated in 37. The controller is connected to the probe, 34 through the circuit illustrated schematically at 40, and to the microwave source through the circuit schematically illustrated at 41. FIG. 1 illustrates that the apparatus can be used to control the application of microwave power to the cavity by moderating the power at the source 11, or where desired or necessary, the microwaves can be moderated by moderating their passage from the source 11 to the cavity 15. FIG. 1 illustrates such moderating means at 42 and the controller is connected to these through the circuit illustrates at 43. The operation of controllers to produce output signals in response to input information such as temperature as well understood in the electronic and computer arts and will not otherwise be described in detail. Exemplary controllers and their method of operation are set forth, for example, in Dorf, *The Electrical Engineering Handbook*, Second Edition, CRC Press (1997). Similarly, means for moderating the passage of microwaves based on controlling them between the source and their destination are generally well understood, with a particularly newer and unique method being set forth in commonly assigned U.S. patent application Ser. No. 08/538,715, filed Oct. 3, 1995, for "Microwave Apparatus for Controlling Power Levels in Individual Multiple Cells," now Pat. No. 5,607,362.

FIG. 2 illustrates the positioning of the silicon carbide susceptors referred to above. Consistent with FIG. 1, FIG. 2 shows the housing 12 and the insulation 21 and 23 that forms a portion of the furnace cavity 13. FIG. 2 also shows two additional pieces of insulation 44 and 45 that were not visible in the view of FIG. 1, along with the sample holder 14 and sample 15. FIG. 2 further illustrates the silicon carbide susceptors 46 and 47 the number and position of which, as noted above, can be selected as desired or necessary to heat the sample. In preferred embodiments, the size and number of the silicon carbide susceptors are sufficient, when subjected to microwave radiation from the source, to raise the temperature inside the furnace cavity to, and maintain the temperature at, about 540° C. even in the absence of any sample.

Because asphalt-aggregate compositions can vary so widely depending on a variety of factors, objective determinations of post-combustion aggregate quality can be difficult. Nevertheless, the appearance of the post-combustion aggregate can provide a qualitative measure of the success of the method in preserving the aggregate as closely as possible to its pre-combustion condition. In this regard, the post-combustion samples from asphalt aggregate compositions analyzed according to the present invention give every indication of being in better—i.e. close or identical to pre-combustion—condition that samples analyzed using more conventional ignition techniques. It is thus expected that any objective evaluation of such post-combustion samples will similarly demonstrate the advantages of the present invention in properly preserving the aggregate.

In summary, the invention provides a more controllable method of carrying out an ignition and combustion analysis of asphalt-aggregate compositions and does so in a manner that minimizes or avoids the degradation of the aggregate that is commonly observed in conventional ignition and combustion testing.

In the drawings and specification, there have been disclosed typical embodiments of the invention, and, although specific terms have been employed, they have been used in a generic and descriptive sense only and not for purposes of limitation, the scope of the invention being set forth in the following claims.

That which is claimed is:

1. A method of analyzing the asphalt content of asphalt-aggregate compositions comprising:

directing microwave radiation from a source to a sample of an asphalt-aggregate composition housed within a cavity until the composition ignites;

drawing air through the cavity:

measuring the temperature of the ignited sample during combustion;

moderating the microwave radiation directed to the sample or the draw of air or both based on the measured temperature to maintain the temperature of the ignited sample within a controllable range; and thermally reducing the gaseous combustion byproducts substantially to carbon dioxide and water vapor as the combustion byproducts exit the cavity.

2. An analysis method according to claim 1 wherein the step of reducing the byproducts comprises carrying out a follow-up combustion step on the gaseous byproducts.

3. A method according to claim 1 wherein the step of moderating the draws of air comprises controlling the airflow to the sample to thereby control the combustion following ignition.

4. A method according to claim 3 comprising decreasing the airflow to discourage overly rapid combustion and thereafter increasing the airflow to encourage slower combustion.

5. A method according to claim 1 wherein the step of moderating the microwave radiation comprises moderating the amount of microwaves produced at the source.

6. A method according to claim 1 wherein the step of moderating the microwave radiation comprises moderating the passage of microwaves between the source and the sample.

7. An apparatus for analyzing the asphalt content of asphalt-aggregate compositions, said apparatus comprising:
   a source of microwave radiation;
   a cavity in communication with said microwave source;
   a sample holder in said cavity for holding a sample of an asphalt-aggregate composition during exposure to microwaves from said source;
   a susceptor within said cavity furnace for converting microwave radiation into heat;
   thermal insulation between said sample holder and the remainder of said cavity for defining a furnace within said cavity;
   means for minimizing or eliminating any undesired combustion products generated by the burning asphalt;
   a temperature sensor for determining the temperature within said thermal insulation;
   means for controlling the microwave power applied to the sample based on the temperature detected by said temperature sensor; and
   means for moderating the airflow through said cavity in response to the measured temperature.

8. An asphalt analyzing apparatus according to claim 7 wherein said source comprises a magnetron.

9. An asphalt analyzing apparatus according to claim 7 wherein said sample holder further comprises a balance for measuring the weight of the sample in said sample holder.

10. An asphalt analyzing apparatus according to claim 7 wherein said controlling means controls the production of microwaves at said source.

11. An asphalt analyzing apparatus according to claim 7 wherein said controlling means controls the passage of microwaves between said source and the sample.

12. An asphalt analyzing apparatus according to claim 7 wherein said combustion byproduct minimizing means comprises:
   an afterburner in fluid communication with said cavity; and;
   means for directing the combustion products from said cavity to said afterburner.

13. An asphalt analyzing apparatus according to claim 12 wherein said directing means comprises:
   an opening in said cavity in fluid communication with said sample holder;
   a duct in communication with the downstream portion of said afterburner; and
   a fan associated with said duct and downstream from said afterburner for drawing ambient air into said cavity and the afterburner products away from said afterburner.

14. An asphalt analyzing apparatus according to claim 13 wherein said afterburner comprises a resistance-heated tubular furnace.

15. An asphalt analyzing apparatus according to claim 7 wherein said thermal insulation is heat resistant, microwave transparent and has a low thermal conductivity.

16. An asphalt analyzing apparatus according to claim 15 wherein said insulation comprises an open cell quartz.

17. An asphalt analyzing apparatus according to claim 7 wherein said susceptor comprises silicon carbide.

18. An asphalt analyzing apparatus according to claim 7 comprising a plurality of susceptors in said cavity furnace.

19. An asphalt analyzing apparatus according to claim 7 wherein said sample holder is perforated to permit air to flow more freely though said sample during combustion.

* * * * *